(12) United States Patent
Zalit et al.

(10) Patent No.: US 10,195,143 B2
(45) Date of Patent: Feb. 5, 2019

(54) DEVICES AND METHODS FOR PREPARING GASTRORETENTIVE DOSAGE FORMS

(71) Applicant: Clexio Biosciences Ltd., Jerusalem (IL)

(72) Inventors: Ilan Zalit, Rosh Ha'ayin (IL); Avshalom Ben Menachem, Zur Izhak (IL)

(73) Assignee: Clexio Biosciences Ltd., Jerusalem (IL)

( * ) Notice: Subject to any disclaimer, the term of this patent is extended or adjusted under 35 U.S.C. 154(b) by 55 days.

(21) Appl. No.: 15/368,274

(22) Filed: Dec. 2, 2016

(65) Prior Publication Data

US 2017/0157043 A1    Jun. 8, 2017

(30) Foreign Application Priority Data

Dec. 2, 2015  (EP) ..................... 15197410

(51) Int. Cl.
*A61K 9/00* (2006.01)
*A61K 9/48* (2006.01)
*A61J 3/07* (2006.01)

(52) U.S. Cl.
CPC ............... *A61K 9/0065* (2013.01); *A61J 3/07* (2013.01); *A61K 9/4808* (2013.01)

(58) Field of Classification Search
None
See application file for complete search history.

(56) References Cited

U.S. PATENT DOCUMENTS

| | | | |
|---|---|---|---|
| 4,767,627 A | 8/1988 | Caldwell et al. | |
| 2014/0360132 A1* | 12/2014 | Tsabari | A61J 3/071 53/122 |

FOREIGN PATENT DOCUMENTS

| | | |
|---|---|---|
| EP | 0202159 | 11/1986 |
| WO | WO 2007/136735 | 11/2007 |
| WO | WO 2015/187746 | 12/2015 |

\* cited by examiner

*Primary Examiner* — Carlos A Azpuru
*Assistant Examiner* — Casey S Hagopian
(74) *Attorney, Agent, or Firm* — Baker & Hostetler LLP

(57) ABSTRACT

The present disclosure provides a device for self-preparation of a gastroretentive dosage form being capable of transitioning between a collapsed configuration and an expanded configuration, the device comprising an assembly unit including: a compartment configured for accommodating the gastroretentive dosage form in the expanded configuration; and a mechanical system configured for, upon operation of an actuation mechanism: (a) transitioning said gastroretentive dosage form into the collapsed configuration; and (b) locking said collapsed gastroretentive dosage form into the collapsed configuration; wherein the device is configured for being portable.

26 Claims, 4 Drawing Sheets

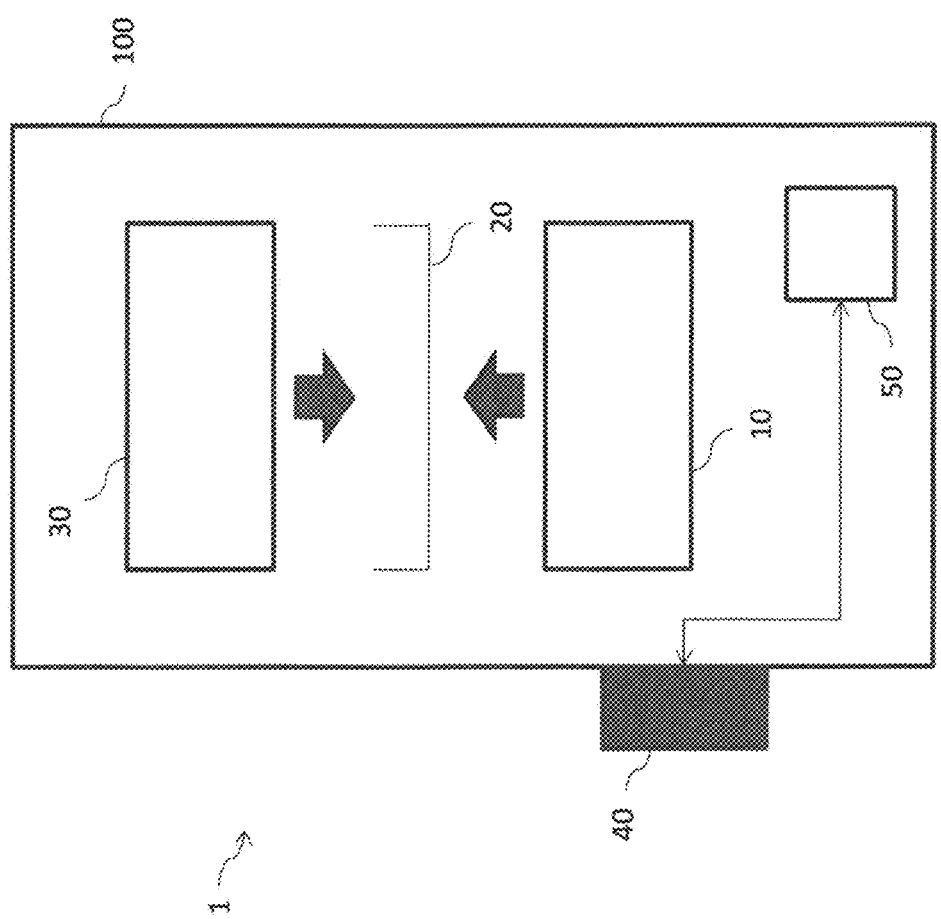

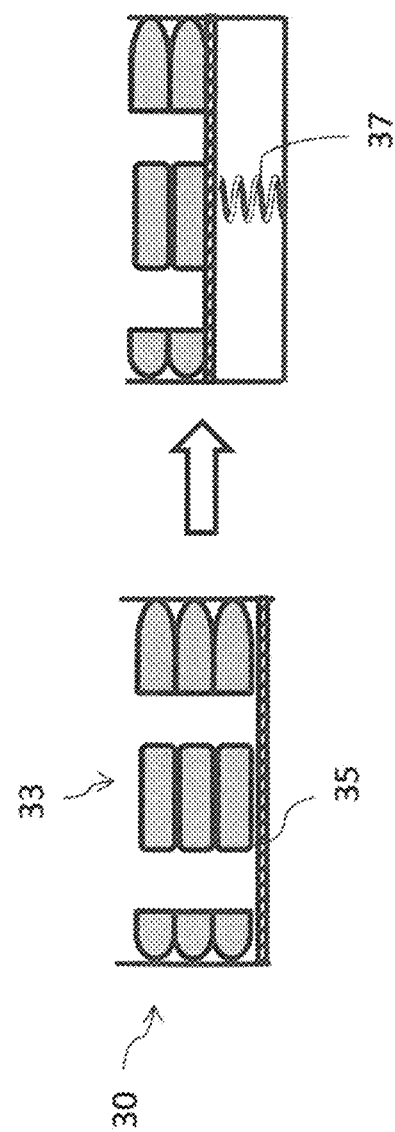

DEVICES AND METHODS FOR PREPARING GASTRORETENTIVE DOSAGE FORMS

CROSS-REFERENCE TO RELATED APPLICATIONS

The present application claims the benefit of priority to European Application No. 15197410.2, filed Dec. 2, 2015, the entire contents of which are incorporated herein by reference.

TECHNOLOGICAL FIELD

The present disclosure relates generally to the field of pharmaceutical products. More particularly, the present disclosure relates to methods and apparatuses useful for preparing an expandable gastroretentive dosage form.

BACKGROUND

Expandable gastroretentive systems and dosage forms are generally prepared in a configuration suitable for ingestion (e.g. folded and fitted into an erodible confining element such as a capsule). After ingestion and erosion of the confining element, the gastroretentive dosage form expands in the stomach into an effective acting shape suitable for stomach retention (e.g. out of the capsule and unfolded) and eventually reduces size to pass through the pylorus or disintegrate.

There are many challenges in designing expandable gastroretentive dosage forms. One example is shelf life and storage limitation. Indeed, expandable gastroretentive dosage forms generally use elastic or semi-elastic materials to enable the shape changing from the effective swallowing configuration to the effective acting shape. However, maintaining stable physical properties of the elastic or semi-elastic materials during product shelf life is a major challenge because deterioration of the elastic capabilities directly impacts the ability to expand into the effective acting shape.

GENERAL DESCRIPTION

The present disclosure provides systems and methods for preparing (e.g. folding and encapsulating) gastroretentive dosage form at the point of care which alleviate at least in part the limitations of the prior art techniques and in particular the storage limitation issue. The teachings of the present disclosure may apply to various types of gastroretentive dosage forms and particularly apply to the gastroretentive dosage forms disclosed in patent application PCT/US15/033850 which is hereby incorporated by reference.

In the present application, the following terms and their derivatives may be understood in light of the below explanations:

It is understood that the term "gastroretentive dosage form" (GRDF) may refer to gastroretentive systems or forms with expanding geometry i.e. expandable gastroretentive dosage forms. The different embodiments of the expandable GRDF described in the related patent application PCT/US15/033850 are hereby specifically incorporated by reference. In general, expandable gastroretentive dosage forms may be prepared in a configuration suitable for swallowing. In the following, the term "preparation" may be used to refer to the actions of collapsing and subsequent locking of a GRDF in the collapsed configuration. Locking of the GRDF into the collapsed configuration may be performed in different ways depending on the type of GRDF. In such a prepared state, the gastroretentive dosage form is maintained (locked) in collapsed configuration by an erodible retention mechanism. The retention mechanism may be an erodible confining element. For example, the collapsed GRDF may be encapsulated into a capsule. Hence, a "prepared" gastroretentive dosage form may be in a configuration suitable for swallowing. The prepared expandable GRDF may be released from the retention mechanism after the gastric fluids dissolve the retention mechanism and may thereby be operative to expand in the stomach in order to prevent gastric emptying. The expanded GRDF is thereby capable of residing in the confines of the stomach for the purpose of providing a platform for the controlled release of biologically active agents or diagnostic formulations. It is noted that for the purpose of the present description of the preparation/cocking device, the term gastroretentive dosage form may refer to a dosage form which is not prepared. With reference to FIGS. 1A-1B, in some embodiments of the present disclosure, the gastroretentive dosage form 70 may include two arms 71 releasably connected to each other by a hinge assembly 73, wherein the two arms 71 are capable of pivoting about the hinge assembly 73 from a collapsed configuration, as shown in FIG. 1B into an expanded configuration, as shown in FIG. 1A. The GRDF 70 may be configured so that the arms 71 and hinge assembly 73 disassemble and/or disintegrate at the end of a predetermined time period or upon occurrence of a mechanical event, thereby enabling passage through the pyloric valve of the stomach. It is noted that in some embodiments, the gastroretentive dosage form may include more than two arms and the device disclosed hereinbelow may be configured for preparing a gastroretentive dosage form including more than two arms.

In the collapsed configuration, the GRDF 70 may have dimensions enabling encapsulation into a pharmaceutical capsule. In some embodiments, other type of erodible confining elements may be used to maintain (i.e. lock) the GRDF 70 into the collapsed configuration. For example, a ring-shape bond made of an erodible material may be applied to the gastroretentive dosage form so as to enclose the arms 71. In some other embodiments, the arms 71 may comprise a fastening connection engageable when the GRDF is in the collapsed configuration, thereby enabling locking of the GRDF into the collapsed configuration. For example, an erodible snap fit connection (not shown) may be formed in the arms 71, for example at the free end of the arms 71. In some embodiments, the fastening connection may be formed by applying an erodible adhesive/chemical bonding on an inner surface of the arms 71 so that when the arms 71 are brought together the adhesive or chemical bonding maintains the GRDF 70 in the collapsed configuration. In some embodiments, the arms 71 and/or hinge assembly 73 may be configured to eventually degrade in the stomach. In other embodiments, the arms 71 and/or the hinge assembly 73 may be configured to retain their size and shape in the stomach, but, once disassembled, are easily passable through the pyloric valve.

The two arms 71 may be made of any combination of active pharmaceutical ingredients (APIs), diagnostic devices or materials and/or various excipients and polymers. In some embodiments, at least one of the arms 71 may include one or several substantially hollow cavities defined therein which may be configured to receive (enclose) one or several insert(s). The insert(s) may include any combination of active pharmaceutical ingredients (APIs), diagnostic devices or materials and/or various excipients and polymers. The GRDF 70 may be configured to facilitate erosion or dissolution of the insert(s) (which releases the API) in a predetermined manner or along a particular erosion pathway. For example, exposure of the insert(s) to the gastric fluids may be controlled by providing one or more openings in the one or more cavities receiving the insert(s). In some embodiments, release or erosion of the insert may facilitate mechanical disassembly of the GRDF 70. For example, the GRDF 70 may be configured so that the inserts in the cavities of the arms 71 participate in the mechanical engagement between the hinge assembly 73 and the arms 71 so that once the inserts have sufficiently eroded the hinge assembly 73 and the arms 71 detach.

The hinge assembly 73 may be unitary or may include several components. The connection between the arms 71 and the hinge assembly 73 may be accomplished by adhesive/chemical bonding or by any known mechanical engagement. The hinge assembly may be made of an elastic polymer.

Optionally, the gastroretentive dosage form 70 may further include a biasing element 75 configured to bias the two arms 71 into the expanded configuration. The biasing element 75 may be made of an elastic polymer. Once the GRDF 70 is expanded within the stomach, biasing element 75 may be configured to prevent the two arms 71 from returning to the collapsed configuration. In some embodiments, biasing element 75 may be integral with one of the two arms 71 and elastically deformable relative thereto. In some embodiments, the biasing element 75 may further be configured to engage a corresponding slot defined within the other of the two arms 71 to maintain the two arms in the expanded configuration and prevent the two arms 71 from returning to the collapsed configuration. In some embodiments, the biasing element 75 may be omitted and the hinge assembly 73 may be formed of a shape memory material such as polylactic acid or a shape memory alloy such as Nitinol®, which is configured to prevent arms 71 from returning to the collapsed configuration.

As used herein, the term "collapsed configuration" of the GRDF is that state where the GRDF is in a folded state. In the folded state, the GRDF may have a size suitable for application of a retention mechanism such as a pharmaceutical capsule and/or for swallowing.

As used herein, the term "expanded configuration" of the GRDF is that state after ingestion and erosion of the retention mechanism which is capable of maintaining the GRDF in the stomach (gastric retention) and preventing passage through the pyloric valve. In the present disclosure, the expanded configuration is also the storage state of the GRDF prior to preparation (cocking).

As used herein, the term "arm" or "arms" may include any structure that includes a length, width and thickness and aids in achieving size for gastric retention. In some embodiments, an arm may refer to an elongated body extending mainly along a longitudinal axis direction. In some embodiments of the present disclosure, an arm as described herein may retain an active pharmaceutical or diagnostic. In some embodiments of the present disclosure, an arm may define a cavity therein configured to retain an insert or pharmaceutical tablet (made from one or more APIs, diagnostics, excipients and/or polymers).

As used herein, the term "hinge assembly" includes any mechanism adapted to permit relative movement—and in particular pivotal movement—between two or more structures. In some embodiments of the present disclosure, a hinge assembly of a GRDF may be provided to permit relative movement between two (or optionally more) arms of a GRDF. The hinge assembly may consist of one integral part or of several parts. The hinge assembly may be durable in the stomach for a period of time, and it may attach to the arms in both the collapsed and expanded configurations. The hinge assembly may be capable of, at a predetermined time or upon occurrence of a mechanical event, disengaging from the one or more arms.

As used herein, the term "mechanical event" may be any event that changes the physical properties of one or more structures over time or upon contact with another material or fluid, e.g., gastric fluid inside the body. Absorption, dissolution, melting, degradation, erosion, pH change or temperature change, etc. are all examples of mechanical events.

As used herein, an "erodible" material may comprise any material that degrades upon introduction to a specified environment or upon contact with a specified material or fluid e.g. a gastric environment or gastric fluid.

The term "dosing unit" may refer to a system consisting of a gastroretentive dosage form and a retention mechanism (e.g. a capsule i.e. a capsule body and head). It is noted that for the purpose of the present description, the term dosing unit may refer to a non-prepared entity. In other words, in a dosing unit the GRDF may not be locked i.e. the retention mechanism may not be applied to the GRDF. As explained below, in some embodiments of the present disclosure, a magazine unit may store one or more dosing units, the gastroretentive dosage forms being in an expanded configuration.

The term "gastric retention" may refer to the maintenance or holding of a pharmaceutical in the stomach, for a time longer than the time it would have retained in the stomach when delivered in a free form or within a gastro-intestinal delivery vehicle which is not considered gastroretentive. Gastro-retentivity may be characterized by retention in the stomach for a period that is longer than the normal emptying time from the stomach, such as longer than about 2 hours, in some cases longer than about 3 hours, and in many cases more than about 4, 6, 8 or 10 hours. Gastro-retentivity typically means retention in the stomach for a period of time of about 3, 4, 6, 8, 10, or at times 18 hours, even up to about 21 hours or longer. Gastro-retentivity may also mean retention in the stomach for a predetermined time period of at least 4, 6, 8, 10, 12, and 18 hours.

As used herein, a size "suitable for swallowing" may be any size and/or shape of an encapsulated dosage form that is capable of being swallowed by either a human or an animal.

As used herein, "excipient" may refer to a component, or mixture of components, that is used in the formulation of the compositions or inserts of the present disclosure to give desirable characteristics to the composition or insert.

As used herein, diagnostic or an active pharmaceutical ingredient (API) is meant to include any substance relevant for gastric retention as recognized in the art. A wide variety of APIs (which may be therapeutic, diagnostic or otherwise beneficial) may be employed in accordance with the aspects of the present disclosure. Any API which is relevant for gastric retentive delivery or as a diagnostic known in the arts is intended to be encompassed herein. Relevant APIs are not limited to, but may include the following: APIs acting locally in the stomach; APIs primarily absorbed in the stomach; APIs poorly soluble in alkaline pH; APIs with narrow windows of absorption; APIs absorbed rapidly from the GI tract; APIs that degrade in the colon; and APIs that disturb colonic microbes.

Active pharmaceutical ingredients (APIs) may include but are not limited to the following: prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, metformin, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, nifedipine, methazolamide, bendroflumethiazide, chlorpropamide, glipizide, glyburide, gliclazide, tobutamide, chlorproamide, tolazamide, acetohexamide, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-nor-progesterone, norgestrel, norethindrone, norethisterone, norethiederone, progesterone, norgesterone, norethynodrel, terfandine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, selegiline, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine, and pharmaceutical salts of these active agents. Further examples are proteins and peptides which include, but are not limited to, cyclosporins such as cyclosporine A, insulin, coichicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

As used herein, the term "upon exposure to gastric fluid" or under simulated gastric conditions is meant to be taken literally or when needed, based on a suitable model. One example of such a suitable model includes exposure to 400 ml of 0.1N HCl and 150 gram glass beads in a 500 mL dissolution chamber, at 37° C. at 8 RPM. In another model, Xanthan gum 0.125 gr/L, pH2 is at 37° C.

Therefore, in a first aspect, the present disclosure provides a device for self-preparation of a gastroretentive dosage form being capable of transitioning between a collapsed configuration and an expanded configuration, the device comprising an assembly unit including: a compartment configured for accommodating the gastroretentive dosage form in the expanded configuration; and a mechanical system configured for, upon operation of an actuation mechanism: (a) transitioning said gastroretentive dosage form into the collapsed configuration; and (b) locking said collapsed gastroretentive dosage form into the collapsed configuration; wherein the device is configured for being portable.

In some embodiments, the device is configured to prepare a single gastroretentive dosage form upon operation of the actuation mechanism.

In some embodiments, the mechanical system is configured for locking said collapsed gastroretentive dosage form by confining the collapsed gastroretentive dosage form using an erodible confining element.

In some embodiments, the erodible confining element is a capsule and the mechanical system is configured for encapsulating the collapsed gastroretentive dosage form into the capsule.

In some embodiments, the erodible confining element comprises a ring-shaped bond and the mechanical system is configured for applying the ring-shaped bond onto the collapsed gastroretentive dosage form.

In some embodiments, the gastroretentive dosage form comprises an erodible fastening connection engageable in the collapsed configuration and the mechanical system is configured for locking said collapsed gastroretentive dosage form by engaging said fastening connection.

In some embodiments, the compartment is further configured for receiving, upon operation of the actuation mechanism, the gastroretentive dosage form from a magazine unit engageable with the assembly unit.

In some embodiments, the mechanical system may include a movable member configured for travelling within the compartment upon operation of the actuation mechanism and travelling of the movable member participates in transitioning the gastroretentive dosage form into the collapsed configuration.

In some embodiments, the compartment may include a passageway configured for enabling slidable movement of the collapsed gastroretentive dosage form therethrough.

In some embodiments, the compartment includes a passageway configured for enabling slidable movement of the collapsed gastroretentive dosage form therethrough; the mechanical system includes a movable member configured for travelling within the compartment upon operation of the actuation mechanism; and the assembly unit is configured so that, when a gastroretentive dosage form in the expanded configuration is accommodated in the compartment, travelling of the movable member transitions the gastroretentive dosage form into the collapsed configuration by pushing the gastroretentive dosage form into the passageway.

In some embodiments, the passageway includes a releasable stopper and is further configured for accommodating a first capsule section.

In some embodiments, the mechanical system further includes a push member configured for pushing a second capsule section towards the passageway upon operation of the actuation mechanism thereby allowing encapsulation of the collapsed gastroretentive dosage form inserted in the passageway.

In some embodiments, the gastroretentive dosage form comprises: two arms connected together by a hinge assembly and pivotable between the collapsed configuration in which the two arms are disposed in close proximity to each other and the expanded configuration in which the two arms are further apart from each other; and a biasing element configured to maintain the two arms apart when the two arms are in the expanded configuration; and the mechanical system further comprises a disengagement mechanism configured for opening the arms of the gastroretentive dosage form thereby disengaging the biasing element and the two arms.

In some embodiments, the gastroretentive dosage form comprises: two or more arms connected together by at least one hinge assembly, the two or more arms being pivotable between the collapsed configuration in which the two or more arms are disposed in close proximity to each other and the expanded configuration in which the two or more arms are further apart from each other; and a biasing element configured to maintain at least two arms of the two or more arms apart when said at least two arms are in the expanded configuration; and the mechanical system further comprises a disengagement mechanism configured for disengaging the biasing element and said at least two arms.

In some embodiments, the gastroretentive dosage form comprises two arms connected together by a hinge assembly and pivotable between the collapsed configuration in which the two arms are disposed in close proximity to each other and the expanded configuration in which the two arms are further apart from each other; and the compartment comprises a V-shaped portion and an apex of the V-shaped portion opens onto the passageway, the compartment being further configured to accommodate the gastroretentive dosage form in the expanded configuration so that the hinge assembly is fitted at the apex of the V-shaped portion thereby facing an opening of the passageway.

In some embodiments, the device further comprises a gastroretentive dosage form in the expanded configuration accommodated in the compartment.

In some embodiments, the device further comprises a magazine unit configured for storing one or more gastroretentive dosage forms in the expanded configuration, the magazine unit being engaged with the assembly unit and configured for delivering said stored gastroretentive dosage form on the compartment of the assembly unit upon operation of the actuation mechanism.

In some embodiments, the magazine unit is further configured for storing erodible confining elements and for delivering an erodible confining element on the compartment upon operation of the actuation mechanism.

In some embodiments, the magazine unit is disposable.

In some embodiments, the device is configured so that the magazine unit is swappable, in particular by using a detachable connection such as a quick connect termination and/or a bayonet fixing.

In some embodiments, the device further comprises a loading mechanism configured for loading a gastroretentive dosage form in the expanded configuration, and optionally an erodible confining element, from the magazine unit onto the compartment.

In some embodiments, the loading mechanism comprises a spring mounted board arranged in the magazine unit and configured for, upon operation of the actuation mechanism, expelling one gastroretentive dosage form in the expanded configuration and optionally two capsule sections, from the magazine unit onto the compartment.

In some embodiments, the device further comprises mounting means to enable attaching the device to a patient, in particular using a belt attachment loop.

In some embodiments, the device further comprises an electronic unit configured for recording data indicative of the use of the device.

In some embodiments, the device further comprises a sensor module including positional sensors configured for recording positional data indicative of a position and/or orientation of the device during use of the device.

In some embodiments, the electronic unit further comprises a communication module configured for transmitting recorded data to an interface platform.

In some embodiments, the device further comprises an alarm unit configured for emitting an alarm sound and/or a visual signal when a predetermined time period has elapsed after preparation of a gastroretentive dosage form.

In some embodiments, the electronic unit comprises a microchip with an addressable register for storing, communicating and transferring the recorded data.

In a further aspect, the present disclosure also provides a magazine unit configured for storing one or more gastroretentive dosage forms in the expanded configuration, and optionally erodible confining elements, the magazine unit being configured for engaging with the device according to any one of the preceding claims and for delivering one of said stored gastroretentive dosage form, and optionally one of said stored erodible confining element, on the compartment of the assembly unit upon operation of the actuation mechanism.

In some embodiments, the magazine unit further comprises a base board on which the one or more gastroretentive dosage forms, and optionally the erodible confining elements, are piled, the base board being configured for, upon operation of the actuation mechanism, expelling one gastroretentive dosage form in the expanded configuration, and optionally one erodible confining element, onto the compartment.

In some embodiments, each erodible confining element comprises two capsule sections.

In a further aspect, the present disclosure also provides a method of preparing a gastroretentive dosage form, the gastroretentive dosage form being capable of transitioning between a collapsed configuration and an expanded configuration, the method comprising: (a) transitioning said gastroretentive dosage form into the collapsed configuration; (b) locking said collapsed gastroretentive dosage form into the collapsed configuration; wherein steps (a)-(b) are performed by a patient prior to self-administration of the prepared gastroretentive dosage form.

In some embodiments, locking said collapsed gastroretentive dosage form comprises confining the collapsed gastroretentive dosage form using an erodible confining element such as a capsule.

In some embodiments, steps (a) and (b) are performed using a portable device as previously described.

In some embodiments, the method further comprises swallowing the prepared gastroretentive dosage form.

In some embodiments, swallowing the prepared gastroretentive dosage form is performed immediately after the locking of the collapsed gastroretentive dosage form.

In some embodiments, swallowing the prepared gastroretentive dosage form is performed within 10 minutes of the locking, preferably within 3 minutes.

In some embodiments, the method comprises the steps of: releasing the gastroretentive dosage form in the expanded configuration onto the compartment of a device as previously described; collapsing the gastroretentive dosage form into a densely packed configuration; pushing said collapsed gastroretentive dosage form into a capsule section; conjoining said capsule section with another capsule section thereby encapsulating said collapsed gastroretentive dosage form into the two capsule sections.

In a further aspect, the present disclosure provides a computer program for monitoring preparation of a gastroretentive dosage by a device including an electronic unit as previously described, wherein the computer program comprises software code which, when executed on a processing module of the electronic unit, is adapted to perform the steps of: recording data indicative of an operation of the actuation mechanism; storing said data in an addressable register of a microship of the electronic unit; transferring said data to an interface platform for analysis and/or health data management.

In a further aspect, the present disclosure also provides a prepared gastroretentive dosage form comprising an effective amount of drug formulation for the treatment of a medical disorder and configured for an extended release and/or prolonged delivery of an included drug formulation, wherein the gastroretentive dosage form is prepared using a device as previously described or by performing the method as previously described.

In a further aspect, the present disclosure provides a method for the treatment of medical disorders by a gastroretentive dosage form containing a patient specific dosage of a drug product, configured for prolonged delivery and/or extended release of the drug product, said gastroretentive dosage form being prepared by performing the method previously described.

In some embodiments, the preparation is performed within 24 hours of the administration of the gastroretentive dosage form, preferably within 10 to 30 minutes, most preferably within 3 to 5 minutes.

In a further aspect, the present disclosure provides a method of immediate packaging prior to use for a pharmaceutical, in particular with the ability to obtain feedback from the patient or doctor for personalized medicine. Further, the present disclosure provides for a portable device for self-packaging (e.g. encapsulation) at the point of care of a pharmaceutical product configured for immediate packaging prior to use of a pharmaceutical product.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 2 is a functional block diagram illustrating generally a device according to embodiments of the present disclosure.

FIG. 4 illustrates a magazine unit according to embodiments of the present disclosure.

For the sake of clarity, similar references may indicate similar elements on the figures.

DETAILED DESCRIPTION OF ILLUSTRATIVE EMBODIMENTS

Figure 1B:
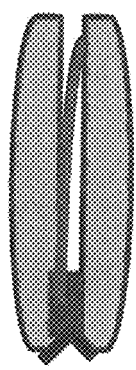
FIG. 1A-1B, already described, illustrate an exemplary gastroretentive dosage form according to embodiments of the present disclosure.

Described herein are some examples of systems and methods useful for encapsulation of expandable gastroretentive dosage forms.

In the following detailed description, numerous specific details are set forth in order to provide a thorough understanding of the subject matter. However, it will be understood by those skilled in the art that some examples of the subject matter may be practiced without these specific details. In other instances, well-known methods, procedures and components have not been described in detail so as not to obscure the description.

As used herein, the phrase "for example," "such as", "for instance" and variants thereof describe non-limiting examples of the subject matter.

Reference in the specification to "one example", "some examples", "another example", "other examples, "one instance", "some instances", "another instance", "other instances", "one case", "some cases", "another case", "other cases" or variants thereof means that a particular described feature, structure or characteristic is included in at least one example of the subject matter, but the appearance of the same term does not necessarily refer to the same example.

It should be appreciated that certain features, structures and/or characteristics disclosed herein, which are, for clarity, described in the context of separate examples, may also be provided in combination in a single example. Conversely, various features, structures and/or characteristics disclosed herein, which are, for brevity, described in the context of a single example, may also be provided separately or in any suitable sub-combination.

Unless specifically stated otherwise, as apparent from the following discussions, it is appreciated that throughout the specification discussions utilizing terms such as "generating", "determining", "providing", "receiving", "using", "performing", "transmitting", "recording", "or the like, may refer to the action(s) and/or process(es) of any combination of software, hardware and/or firmware. For example, these terms may refer in some cases to the action(s) and/or process(es) of a programmable machine, that manipulates and/or transforms data represented as physical, such as electronic quantities, within the programmable machine's registers and/or memories into other data similarly represented as physical quantities within the programmable machine's memories, registers and/or other such information storage, transmission and/or display element(s).

FIG. 2 is a functional block diagram which illustrates schematically general elements of an encapsulation device 1 according to embodiments of the present disclosure.

The device 1 generally comprises an assembly unit 100 including a mechanical system 10 cooperating with a compartment 20 configured for accommodating a gastroretentive dosage form (GRDF) in an expanded configuration. The device 100 further includes an actuation mechanism 40 upon operation of which the mechanical system 10 is operative for transitioning the GRDF accommodable on the compartment from the expanded configuration into the collapsed configuration and successively for locking said collapsed gastroretentive dosage form into the collapsed configuration. As explained above, the locking of the collapsed GRDF may be performed using a retention mechanism. The retention mechanism may be an erodible confining element separate from the GRDF such as a capsule or a ring-shaped bond. In these embodiments, the mechanical system 10 may be configured for applying the erodible confining element to the collapsed GRDF to lock the GRDF in the collapsed configuration. For example, the locking step may comprise encapsulating the collapsed GRDF into a capsule. In some other embodiments, the retention mechanism may be embedded with the GRDF. For example, the GRDF may comprise an erodible fastening connection engageable when the GRDF is in the collapsed configuration. In these embodiments, the mechanical system 10 may be configured for engaging said fastening connection.

The actuation mechanism may include a push button. In contrast with mass production systems, the cocking device 1 is a portable device and is configured to operate on a retail basis. The assembly unit 100 may be housed in a housing. The housing may have such dimensions and weight so as to be easily portable. For example, a respective height, width and depth of the device may roughly be between 3-10 cm by 3-10 cm by 3-10 cm, for example 5 cm by 10 cm by 3 cm. The mechanical system and the compartment may be positioned adjacent to each other. The mechanical system 10 may be an automated robotic system. The device may include a power source such as a battery. The device disclosed in the present disclosure enables a patient to self-prepare a GRDF on-demand at the point of care. Therefore, a user (patient) may prepare the GRDF before administration thereby avoiding the need for storing a collapsed GRDF for long time periods and the issues linked with loss of elastic properties which are linked with maintaining a GRDF in the collapsed configuration. Indeed, the shelf life of a GRDF in the expanded configuration may be of around 1 to 3 years. The device according to the present disclosure may comprise mounting means to enable attaching the device to a user, for example a belt attachment loop. This enables the device to be easy to carry for allowing easy home and outdoor use. The device according to the present disclosure may be simple to use and adapted for physically disabled patients.

In some embodiments, the mechanical system 10 may include engagement means for transitioning and/or folding the GRDF. The engagement means configured for transitioning and/or folding the gastroretentive dosage form may be in the form of a movable post and/or wall acting on the outer circumference of the dosage form thus pushing the dosage form in a first movement into a circumferential clamping arrangement with said compartment, collapsing, in particular folding the dosage form in a second movement, and wherein by a third movement of the engagement means said collapsed gastroretentive dosage form is being encapsulated into a capsule section, and wherein by a fourth movement of the engagement means the two capsule sections are conjoined. In some embodiments, the compartment wall or parts of a compartment wall may be movable to engage and/or to act on the outer circumference of the gastroretentive dosage form and the engagement means may comprise a non movable clamping fixture for encapsulation.

In some embodiments, the device 1 may include a single dosage unit i.e. a retention mechanism (e.g a capsule head and body) and a gastroretentive dosage form in the expanded configuration accommodated in the compartment 20. Such encapsulation device may be disposable and adapted for single use.

In some embodiments, the assembly unit 100 may be configured so that a magazine unit 30 configured for storing one or more GRDF in the expanded configuration and optionally erodible confining elements (e.g. capsule heads and bodies) may be engageable therewith. The magazine unit 30 may have variable sizes i.e. contain different amount of expanded GRDF and optionally confining elements. For example, the magazine unit 30 may contain 1 to 100 expanded GRDF (and optionally the same number of capsule heads and bodies), preferably 3, 5, 10, 20.

In some embodiments, the device 1 may include the magazine unit 30 engaged with (inserted into) the assembly unit 100 as represented schematically on FIG. 2. The magazine unit 30 may be configured for delivering said stored GRDF in the expanded configuration (an optionally a confining element such as a capsule) on the compartment 20 of the assembly unit 100. The delivery of a GRDF in the expanded configuration (and optionally of the confining element e.g. two capsule sections) from the magazine unit 30 on the compartment 20 may be actuated by the actuation mechanism 40 as a preliminary step before the GRDF transitioning operation. In the embodiments in which the device is configured to cooperate with a magazine unit 30, the device may include a loading mechanism for loading an expanded GRDF and optionally a confining element (e.g. capsule) from the magazine unit 30 onto the compartment 20. As explained below, the loading mechanism may be at least partly incorporated in the magazine unit 30.

The magazine unit 30 may be engaged with the assembly unit 100 so that a delivery area 33 (referenced on FIG. 3) of the magazine unit 30 faces a receiving area of the compartment which receives the expanded GRDF and optionally a confining element (e.g. a capsule body and head). The magazine unit 30 and compartment 20 may be configured so that delivery of an expanded GRDF from the magazine unit 30 on the compartment 20 can be operated by releasing the GRDF (and optionally the confining element) from the magazine unit 30 onto the compartment 20. In other words, the geometry of the magazine unit 30 and compartment 20 may match so that, when the magazine unit 30 is facing the compartment—for example by being engaged so that the magazine delivery area 33 is held on top of the compartment receiving area—delivery of the expanded GDRF can be carried out by discharging an expanded GRDF (and optionally the confining element) from the magazine unit 30. In these embodiments, the loading mechanism may include an release mechanism configured for releasing an expanded GRDF in the magazine so that it can be discharged (dropped) onto the receiving area of the compartment 20. The compartment 20 may be shaped/adapted to the outer shape of the expanded GRDF i.e. sized and shaped for positive fitting and/or force fitting of the expanded GRDF.

As mentioned hereinabove, the magazine unit 30 may further be configured for storing confining elements (e.g. capsule heads and bodies) and for delivering one confining element (e.g. one capsule head and one capsule body) onto the compartment upon operation of the actuation mechanism 40. The magazine unit 30 may be disposable. The device 1 may be configured for allowing the magazine unit 30 to be swapped. For example, the magazine unit 30 may be connectable to the device 1 using a detachable connection such as a quick connect termination and/or a bayonet fixing.

With reference to FIG. 4, the magazine unit 30 may be configured to store the expanded GRDFs as a pile and to operate as a detachable box magazine. In some embodiments, the magazine unit 30 may be configured to store complete dosing units. In some embodiments as shown on FIG. 4, the magazine unit 30 may be configured to store expanded GRDFs, capsule bodies and heads as a pile on a base board 35, wherein each layer of the pile includes a capsule body, an expanded GRDF and a capsule head. In some embodiments, the base board 35 may be mounted on a spring 37 and act as a loading mechanism. The spring mounted board 35 may be configured for expelling one expanded GRDF stored in the magazine unit 30 onto the compartment 20 upon operation of the actuation mechanism 40. In some embodiments, the base board 35 may be operated mechanically without a spring. For example, the base board 35 may be operated using a snail lead mechanism.

Returning to FIG. 2, the device 1 may include an electronic unit 50. The electronic unit 50 may be integrated at least partly on a microchip. The electronic unit 50 may be configured for collecting data indicative of the use of the device and optionally for communicating said data to a remote interface platform. The electronic unit 50 may include a sensor module, a communication module, a processing module and a memory module, wherein said modules are communicatively coupled.

The sensor module may be configured for detecting actuation of the device for example by detecting operation of the actuating mechanism. In particular, the sensor module may be configured to measure temporal data indicative of the actuation of the device i.e. a time and date associated with each actuation of the device. The sensor module may further include positional sensors configured for sensing a position and/or an orientation of the device. The positional sensors may be configured to sense the position and/or the orientation of the device upon operation of the actuation mechanism so as to detect if the device is handled correctly. The positional sensor may comprise a positioning capability such as a GPS capability. The positional sensors may include a gyroscope enabling calculation of a rotational change of the device. The positional sensors may also include an accelerometer operative to determine acceleration and/or speed of the device according to three linear axes. This may enable to measure a motoric condition of the user of the device.

The communication module may be configured for enabling transmission of data from the device to an interface platform. The communication module may communicate directly to the Internet via a wireless connection such as 3G/4G/Wifi/Wimax, etc. The communication module may be configured to communicate with an intermediate electronic device such as a mobile phone. Communication with the intermediate device may be operated using a wireless connection such as a Bluetooth® connection.

The processing module may be any suitable programmable control device and may control the operation of various functions, such as the control of the sensor and communication modules and/or conversion of the sensed data into a different format, as well as other functions performed by the electronic unit and/or device.

The memory module may store software for implementing the various functions of the electronic unit and/or device. The memory module may include one or more storage medium tangibly recording sensor data and program instructions, including for example a hard-drive, permanent memory and semi-permanent memory or cache memory. Program instructions may comprise a software implementation encoded in any computer language.

The device 1 may further include an alarm unit (not shown) configured for emitting an alarm sound and/or a visual signal (for example using a light-emitting diode located on the housing of the device) when a predetermined time period has elapsed after preparation of a gastroretentive dosage form. This may enable to warn a user that an administration time period has ended.

Figure 3:
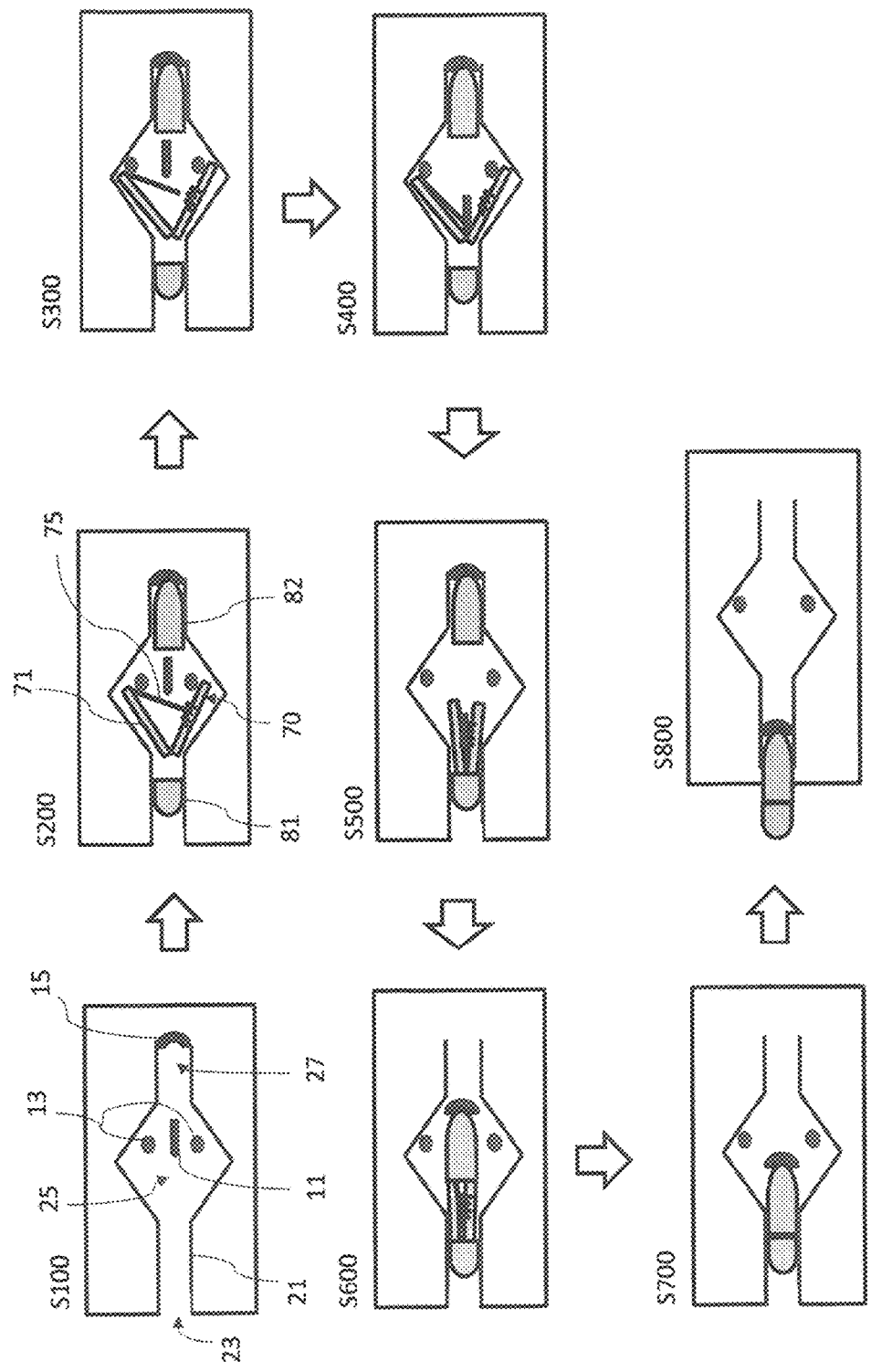
FIG. 3 illustrates an encapsulation process according to embodiments of the present disclosure.

Reference is additionally made to FIG. 3 on which features of the assembly unit 100 are visible in an exemplary embodiment of the device in which locking of the collapsed GRDF is performed by encapsulating the GRDF into a capsule. The encapsulation device may include a compartment 20 which extends substantially along a planar surface. The compartment 20 may include a passageway 21 configured for enabling slidable movement of GRDF in the collapsed configuration. The passageway 21 may include an exit 23 configured for allowing output of an encapsulated GRDF at the end of the encapsulation process as shown with reference to step S800. The compartment 20 may further include a GRDF recess 25 configured for receiving and/or accommodating the expanded GRDF 70. The compartment 20 may include a second capsule section recess 27 configured for accommodating the second capsule section 82. The passageway 21 may define a longitudinal axis of the compartment and the passageway 21, the GRDF recess 25 and the second capsule recess 27 may be aligned and centered with respect to said longitudinal axis. The GRDF recess 25 may include a V-shaped portion wherein an apex of the V-shape portion opens onto the passageway 21.

The mechanical system 10 may comprise a movable member 11 configured for travelling within the compartment upon operation of the actuation mechanism 40. The assembly unit 100 may be configured so that travelling of the movable member 11 transitions the GRDF 70 into the collapsed configuration by pushing the GRDF into the passageway 21. The travelling of the movable member 11 may operate substantially along the longitudinal axis of the passageway 21, towards the passage way 21. In embodiments useful for encapsulating a GRDF including a biasing element, the mechanical system 10 may further comprise a disengagement mechanism 13 configured for opening the arms of the gastroretentive dosage form 70 when the expanded GRDF is accommodated in the compartment and upon operation of the actuation mechanism, thereby disengaging the biaising element 75 and the two arms 71 of the GRDF. The disengagement mechanism may be in the form of two poles as shown on FIG. 2. In some embodiments, the assembly unit 100 may further comprise a releasable stopper (not shown) within the passageway 21 which defines an abutment for receiving a first capsule section 81. The releasable stopper may be configured to be released after conjoining of the capsule sections to allow outputting of the encapsulated GRDF through the exit 23. In some embodiments, the releasable stopper may be a resisting membrane configured to allow passage if a pushing force in the direction of the longitudinal axis exceeds a predetermined threshold. The mechanical system 10 may be configured so that the pushing force on the membrane until the capsule conjoining is below the threshold while the pushing force after the capsule conjoining exceeds said threshold. The mechanical system 10 further may include a push member 15 configured for pushing a second capsule section 82 from the second capsule recess 27 towards the passageway 21 to allow conjoining of the capsule sections (i.e. closing of the capsule). The push member 15 may form a support wall of the second capsule section recess 27.

Figure 1A:
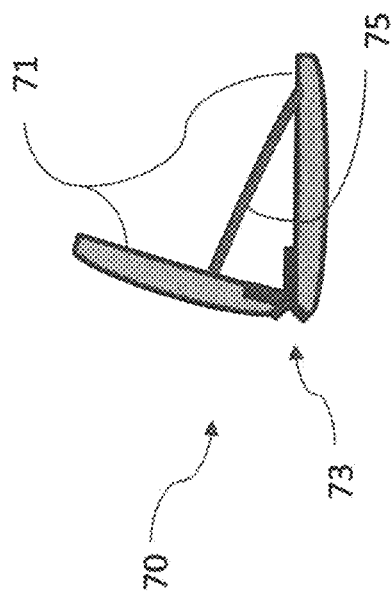

Reference is now made to FIG. 3 which illustrates steps of an automatic self-encapsulation process S100-S800 according to embodiments of the present disclosure. The process steps are for the sake of clarity illustrated on an exemplary embodiment of the device. The illustrated GRDF 70 is of the kind described in relation to FIGS. 1A-1B. It is noted that the features of the encapsulation device described in relation to the illustrated embodiment can be generalized and are distinctly and conjointly applicable to any encapsulation device as encompassed by the present disclosure.

The GRDF 70 includes two arms 71 connected together by a hinge assembly and pivotable between the collapsed configuration in which the two arms are disposed in close proximity to each other and the expanded configuration in which the two arms are further apart from each other and a biasing element 75 configured to maintain the two arms apart when the two arms are in the expanded configuration. The biasing element 75 is insertable in a slot defined in one of the arms 71.

The encapsulation device includes a compartment which extends substantially along a planar surface shown on FIG. 2. The compartment includes a passageway 21 configured for enabling slidable movement of GRDF in the collapsed configuration. The passageway 21 includes an exit 23 configured for allowing output of an encapsulated GRDF at the end of the encapsulation process. The compartment further includes a GRDF recess 25 configured for accommodating the expanded GRDF 70 and a second capsule section recess 27 configured for accommodating the second capsule section 82. The passageway 21 may define a longitudinal axis of the compartment and the passageway 21, the GRDF recess 25 and the second capsule recess 27 are aligned and centered with respect to said longitudinal axis. The GRDF recess 25 includes a V-shaped portion wherein an apex of the V-shape portion opens onto the passageway 21. The GRDF recess 25 may operate a circumferential clamping arrangement of the expanded GRDF 70.

The mechanical system comprises a movable member 11 configured for travelling within the compartment upon operation of the actuation mechanism. The travelling of the movable member 11 operates substantially according to the longitudinal axis of the passageway 21. The mechanical system further comprises a disengagement mechanism 13 in the form of two poles configured for opening the arms of the gastroretentive dosage form 70 when the expanded GRDF is accommodated in the compartment and upon operation of the actuation mechanism, thereby disengaging the biaising element 75 and the two arms 71 of the GRDF. The assembly unit further comprises a releasable stopper (not shown) within the passageway 21 which defines an abutment for receiving a first capsule section 81. The releasable stopper is released after conjoining of the capsule sections to allow outputting of the encapsulated GRDF through the exit 23. The mechanical system further includes a push member 15 configured for pushing a second capsule section 82 towards the passageway 21. The push member 15 forms a support wall of the second capsule section recess 27.

Having generally described some features of the GRDF and of the encapsulation device, operation of the encapsulation device is now described.

In a first step S100, the actuation mechanism of the encapsulation device may be operated by a user who intends to ingest the encapsulated GRDF. The compartment may be empty before operation of the actuation mechanism. Operation of the actuation mechanism may trigger the successive steps S200-S800.

In a second step 5200, a dosing unit i.e. an expanded GRDF 70, a first capsule section 81 (e.g. capsule head) and a second capsule section 82 (e.g. capsule body) may be loaded onto the compartment from the magazine unit. As illustrated, the compartment may be configured for accommodating the first capsule section 81 in the passageway 21, the expanded GRDF 70 in the GRDF recess 25 and the second capsule section 82 in the second capsule recess 27. The expanded GRDF 70 may be accommodated in the GRDF recess 27 so that the hinge assembly of the GRDF 70 is fitted at the apex of the V-shaped portion of the GRDF recess which opens onto the passageway 21, thereby facing the passageway 21.

In a third step S300, the disengagement mechanism 13 may be operated to release the biasing element 75 by opening the arms of the GRDF 70. The poles move outwardly in a direction substantially perpendicular to the longitudinal axis of the passageway 21.

In a fourth step S400, the movable member 11 travels through the GRDF recess 25 along the direction of the longitudinal axis of the passageway 21 thereby swinging the biasing element 75 toward one of the arms 71 and pushing the hinge assembly of the GRDF into the passageway 21, thereby causing closing of the arms 71 of the GRDF 70.

In a fifth step S500, the movable element 11 pursues the travelling movement thereby driving the GRDF into the first capsule section 81 in the passageway 21. At the end of its movement, the movable element 11 is retracted from the compartment e.g. in a plane vertical to the planar surface of the compartment illustrated on FIG. 3. The GRDF 70 may thereby be collapsed into a densely packed (collapsed) configuration.

In a sixth step S600, the push member 15 is activated and drives the second capsule section 82 toward the passageway 21 to conjoin the capsule sections 81, 82. The push member 15 translates along the longitudinal axis of the passageway.

In a seventh step S700, the conjoining of the capsule section is terminated i.e. the capsule is closed. The releasable stopper in the passageway 21 may be retracted and the push member may continue its movement to drive the encapsulated GRDF toward the exit 23.

In an eight step S800, the encapsulated GRDF is exited through the exit 23. The mechanical system may be reset to its starting configuration.

The user may thereafter swallow the encapsulated GRDF. The swallowing of the encapsulated GRDF may be performed immediately after the encapsulation is finished. The swallowing may be performed within 10 minutes of the encapsulation and preferably within 3 minutes of the encapsulation.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It will be appreciated that the embodiments described above are cited by way of example, and various features thereof and combinations of these features can be varied and modified.

While various embodiments have been shown and described, it will be understood that there is no intent to limit the invention by such disclosure, but rather, it is intended to cover all modifications and alternate constructions falling within the scope of the invention, as defined in the appended claims.

What is claimed:

1. A device for self-preparation of a gastroretentive dosage form being capable of transitioning between a collapsed configuration and an expanded configuration, the device comprising an assembly unit including:
   i) a compartment configured for accommodating the gastroretentive dosage form in the expanded configuration; and
   ii) a mechanical system configured for, upon operation of an actuation mechanism:
      (a) transitioning said gastroretentive dosage form into the collapsed configuration; and
      (b) locking said collapsed gastroretentive dosage form into the collapsed configuration;
   wherein the device is configured for being portable.

2. The device according to claim 1, wherein the device is configured to prepare a single gastroretentive dosage form upon operation of the actuation mechanism.

3. The device according to claim 1, wherein the mechanical system is configured for locking said collapsed gastroretentive dosage form by confining the collapsed gastroretentive dosage form using an erodible confining element.

4. The device according to claim 3, wherein the erodible confining element is a capsule and the mechanical system is configured for encapsulating the collapsed gastroretentive dosage form into the capsule.

5. The device according to claim 3, wherein the erodible confining element comprises a ring-shaped bond and the mechanical system is configured for applying the ring-shaped bond onto the collapsed gastroretentive dosage form.

6. The device according to claim 1, wherein the gastroretentive dosage form comprises an erodible fastening connection engageable in the collapsed configuration and the mechanical system is configured for locking said collapsed gastroretentive dosage form by engaging said fastening connection.

7. The device according to claim 1, the compartment being further configured for receiving, upon operation of the actuation mechanism, the gastroretentive dosage form from a magazine unit engageable with the assembly unit.

8. The device according to claim 1, wherein:
(a) the compartment includes a passageway configured for enabling slidable movement of the collapsed gastroretentive dosage form therethrough;
(b) the mechanical system includes a movable member configured for travelling within the compartment upon operation of the actuation mechanism; and
wherein the assembly unit is configured so that, when a gastroretentive dosage form in the expanded configuration is accommodated in the compartment, travelling of the movable member transitions the gastroretentive dosage form into the collapsed configuration by pushing the gastroretentive dosage form into the passageway.

9. The device according to claim 8, wherein the passageway includes a releasable stopper and is further configured for accommodating a first capsule section.

10. The device according to claim 8, wherein the mechanical system further includes a push member configured for pushing a second capsule section towards the passageway upon operation of the actuation mechanism thereby allowing encapsulation of the collapsed gastroretentive dosage form inserted in the passageway.

11. The device according to claim 1, wherein the gastroretentive dosage form comprises:
(a) two or more arms connected together by at least one hinge assembly and pivotable between the collapsed configuration in which the two or more arms are disposed in close proximity to each other and the expanded configuration in which the two arms are further apart from each other; and
(b) a biasing element configured to maintain at least two biased arms of the two or more arms apart when the two or more arms are in the expanded configuration; and
wherein the mechanical system further comprises a disengagement mechanism configured for disengaging the biasing element and the at least two biased arms.

12. The device according to claim 8, wherein:
(a) the gastroretentive dosage form comprises two arms connected together by a hinge assembly and pivotable between the collapsed configuration in which the two arms are disposed in close proximity to each other and the expanded configuration in which the two arms are further apart from each other; and
(b) the compartment comprises a V-shaped portion and an apex of the V-shaped portion opens onto the passageway, the compartment being further configured to accommodate the gastroretentive dosage form in the expanded configuration so that the hinge assembly is fitted at the apex of the V-shaped portion thereby facing an opening of the passageway.

13. The device according to claim 1, further comprising a gastroretentive dosage form in the expanded configuration accommodated in the compartment.

14. The device according to claim 1, further comprising a magazine unit configured for storing one or more gastroretentive dosage forms in the expanded configuration, the magazine unit being engaged with the assembly unit and configured for delivering said stored gastroretentive dosage form on the compartment of the assembly unit upon operation of the actuation mechanism.

15. The device according to claim 14, wherein the magazine unit is further configured for storing erodible confining elements and for delivering an erodible confining element on the compartment upon operation of the actuation mechanism.

16. The device according to claim 14, wherein the magazine unit is disposable.

17. The device according to claim 14, wherein the device is configured so that the magazine unit is swappable via a detachable connection.

18. The device according to claim 14, further comprising a loading mechanism configured for loading a gastroretentive dosage form in the expanded configuration, and optionally an erodible confining element, from the magazine unit onto the compartment.

19. The device according to claim 18, wherein the loading mechanism comprises a spring mounted board arranged in the magazine unit and configured for, upon operation of the actuation mechanism, expelling one gastroretentive dosage form in the expanded configuration and optionally two capsule sections, from the magazine unit onto the compartment.

20. The device according to claim 1, further comprising mounting means to enable attaching the device to a patient.

21. The device according to claim 1, further comprising an electronic unit configured for recording data indicative of the use of the device.

22. The device according to claim 21, further comprising a sensor module including positional sensors configured for recording positional data indicative of a position and/or orientation of the device during use of the device.

23. The device according to claim 21, wherein the electronic unit further comprises a communication module configured for transmitting recorded data to an interface platform.

24. The device according to claim 21, further comprising an alarm unit configured for emitting an alarm sound and/or a visual signal when a predetermined time period has elapsed after preparation of a gastroretentive dosage form.

25. The device according to claim 21, wherein the electronic unit comprises a microchip with an addressable register for storing, communicating and transferring the recorded data.

26. The device according to claim 20, wherein the mounting means uses a belt attachment loop.

* * * * *